(12) United States Patent
Wang et al.

(10) Patent No.: US 9,199,989 B2
(45) Date of Patent: Dec. 1, 2015

(54) N—(IMIDAZOLIDIN-2-YLIDENE)QUINOLINE DERIVATIVES AS MODULATORS OF ALPHA 2 ADRENERGIC RECEPTORS

(71) Applicant: Allergan, Inc., Irvine, CA (US)

(72) Inventors: Liming Wang, Irvine, CA (US); Mohammed I. Dibas, Laguna Niguel, CA (US); Michael E. Garst, Newport Beach, CA (US); Ken Chow, Newport Coast, CA (US); Santosh C. Sinha, Ladera Ranch, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/332,110

(22) Filed: Jul. 15, 2014

(65) Prior Publication Data

US 2014/0329852 A1    Nov. 6, 2014

Related U.S. Application Data

(62) Division of application No. 13/554,546, filed on Jul. 20, 2012, now Pat. No. 8,815,861.

(60) Provisional application No. 61/511,298, filed on Jul. 25, 2011.

(51) Int. Cl.
*A61K 31/4375* (2006.01)
*C07D 471/04* (2006.01)
*C07D 403/12* (2006.01)
*C07D 401/12* (2006.01)

(52) U.S. Cl.
CPC .......... *C07D 471/04* (2013.01); *A61K 31/4375* (2013.01); *C07D 401/12* (2013.01); *C07D 403/12* (2013.01)

(58) Field of Classification Search
CPC .................................................. C07D 471/04
See application file for complete search history.

(56) References Cited

U.S. PATENT DOCUMENTS

| | | |
|---|---|---|
| 3,056,789 A | 10/1962 | Urech |
| 3,890,319 A | 6/1975 | Danielewicz et al. |
| 5,576,437 A | 11/1996 | Cupps |
| 5,739,148 A | 4/1998 | Cupps |
| 5,834,470 A | 11/1998 | Maurer |
| 6,087,361 A | 7/2000 | Munk |
| 6,723,741 B2 | 4/2004 | Jeon |
| 2002/0065307 A1 | 5/2002 | Jeon |

FOREIGN PATENT DOCUMENTS

EP    1285657    2/2003

OTHER PUBLICATIONS

Larry, Wheeler. Surv Ophthalmol. 48:Suppl 1 (2003) S47-S51.*
Shanler, Stuart. Arch Dermatol. 143:11 (2007) 1369-1371.*
Cross, L.C. et al, Rules for the Nomenclature of Organic Chemistry, Section E: Stereochemistry, Pure & Appl. Chem., 1976, 11-30, 45.
Stahl, Heinrich et al, Handbook of Pharmaceutical Salts, Verlag Helvetica Chimica Acta-Zurich, 2002, 329-345.
Terri L Messier, High Throughput Assays of Cloned Adrenergic, Muscarinic, Neurokinin, and Neurotrophin Receptors in Living Mammalian Cells, Pharmacology & Toxicology, 1995, 308-311, 76, US.
Patent Cooperation Treaty, Notification of Transmittal of the International Search Report and the Written Opinion of the International Searching Authority, or the Declaration, Form PCT/ISA/220, Int. App. No. PCT/US2012/047570, Jul. 20, 2012.
Wermuth, Camille G. Molecular Variations Based on Isoteric Replacements. The Practice of Medicinal Chemistry. Academic Press, 1996. pp. 203-237.
FDA. Orange Book: Approved Drug Products with Therapeutic Equivalence Evaluations. Bromonidine Tartrate. Approved May 22, 2006. Online at: http://www.accessdata.fda.gov/scripts/cder/ob/docs/obdetail.cfm?Appl_No=021764& TABLE1 =OB_Rx.

* cited by examiner

*Primary Examiner* — Golam M M Shameem
*Assistant Examiner* — Laura Daniel
(74) *Attorney, Agent, or Firm* — Barbara C. Potts

(57) ABSTRACT

The present invention relates to novel N-(imidazolidin-2-ylidene)quinoline derivatives, processes for preparing them, pharmaceutical compositions containing them and their use as pharmaceuticals.

9 Claims, No Drawings

N—(IMIDAZOLIDIN-2-YLIDENE)QUINOLINE DERIVATIVES AS MODULATORS OF ALPHA 2 ADRENERGIC RECEPTORS

RELATED APPLICATION

This application claims the benefit of U.S. Non Provisional application Ser. No. 13/554,546, filed Jul. 20, 2012, which claims the benefit of U.S. Provisional Application Ser. No. 61/511,298, filed Jul. 25, 2011, the disclosure of which are hereby incorporated in their entirety by reference.

FIELD OF THE INVENTION

The present invention relates to novel N-(imidazolidin-2-ylidene)quinoline derivatives, as alpha 2 adrenergic modulators. Alpha 2 adrenergic receptors have been characterized by molecular and pharmacological methods which include alpha 1A, alpha 1B, alpha 2A, alpha 2B and alpha 2C. Activation of these alpha receptors evokes physiological responses. Adrenergic modulators described in this invention activate alpha 2 receptors and have useful therapeutic actions.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine. Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. Functional differences between $\alpha_1$ and $\alpha_2$ receptors have been recognized, and compounds which exhibit selective binding between these two subtypes have been developed.

U.S. Pat. No. 6,723,741 discloses benzimidazoles and benzothiazoles as alpha 2 adrenergic receptor agonists.

SUMMARY OF THE INVENTION

The present invention relates to novel N-(imidazolidin-2-ylidene)quinoline derivatives, as alpha 2 adrenergic modulators. These novel compounds will be useful for the treatment of mammals, including humans, with a range of conditions and diseases that are alleviated by alpha 2A, 2B, 2C activation, including but not limited to treating glaucoma, elevated intraocular pressure, ischemic neuropathies, optic neuropathy, pain, visceral pain, corneal pain, headache pain, migraine, cancer pain, back pain, irritable bowel syndrome pain, muscle pain and pain associated with diabetic neuropathy, other retinal degenerative conditions, stroke, cognitive deficits, neuropsychiatric conditions, drug dependence and addiction, withdrawal symptoms, obsessive-compulsive disorders, obesity, insulin resistance, stress-related conditions, diarrhea, diuresis, nasal congestion, spasticity, attention deficit disorder, psychoses, anxiety, depression, autoimmune disease, Crohn's disease, gastritis, Alzheimer's, Parkinson's ALS, neurodegenerative diseases, retinal neuroprotection, skin conditions, skin diseases, rosacea, sunburn, psoriasis, acne rosacea, menopause-associated hot flashes, hot flashes resulting from orchiectomyatopic dermatitis, photoaging, seborrheic dermatitis, acne, allergic dermatitis, redness of the skin, treatment of redness and itch from insect bites, flushing and redness associated with hot flashes, erythema associated with hot flashes, telangiectasia (dilations of previously existing small blood vessels) of the face, rhinophyma (hypertrophy of the nose with follicular dilation), red bulbous nose, acne-like skin eruptions (may ooze or crust), burning or stinging sensation, irritated and bloodshot and watery eyes, erythema of the skin, cutenous hyperactivity with dilation of blood vessels of the skin, Lyell's syndrome, Stevens-Johnson syndrome, erythema multiforme minor, erythema multiforme major and/or other inflammatory skin diseases, age related macular degeneration, wet macular degeneration, dry macular degeneration, geographic atrophy, diabetic retinopathy, diabetic macular edema, tumors, wound healing, inflammation and retinal vein occlusion, enhancing vision in patients with vision loss from conditions including glaucoma, retinitis pigmentosa and neuritis secondary to multiple sclerosis.

In one aspect, the invention therefore provides a compound of Formula I, its enantiomers, diastereoisomers, hydrates, solvates, crystal forms and tautomers or a pharmaceutically acceptable salt thereof

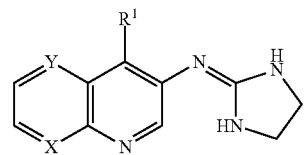

Formula I wherein:
$R^1$ is hydrogen, substituted or unsubstituted $C_{1-8}$ alkyl or halogen;
Y is CH or N;
X is CH or N; and
compound N-(imidazolidin-2-ylidene)quinolin-4-amine;
except compound N-(4,5-dihydro-1H-imidazol-2-yl)-3-quinolinamine.

In another aspect, the invention provides a compound of Formula I wherein:
$R^1$ is hydrogen, methyl, bromine or chlorine;
Y is CH or N; and
X is CH or N;
except compound N-(4,5-dihydro-1H-imidazol-2-yl)-3-quinolinamine.

In another aspect, the invention provides a compound of Formula I wherein:
$R^1$ is methyl, bromine or chlorine;
Y is CH or N; and
X is CH or N.

In another aspect, the invention provides a compound of Formula I wherein:
$R^1$ is methyl, bromine or chlorine;
Y is CH or N; and
X is CH or N.

In another aspect, the invention provides a compound of Formula I wherein:
$R^1$ is methyl;
Y is CH or N; and
X is CH or N.

In another aspect, the invention provides a compound of Formula I wherein:
$R^1$ is bromine;
Y is CH or N; and
X is CH or N.

In another aspect, the invention provides a compound of Formula I wherein:
$R^1$ is chlorine;
Y is CH or N; and
X is CH or N.

In another aspect, the invention provides a compound of Formula I wherein:
$R^1$ is chlorine;
Y is CH or N; and
X is CH.

In another aspect, the invention provides a compound of Formula I wherein:
$R^1$ is chlorine;
Y is CH; and
X is CH or N.

The term "alkyl" as used herein, is defined as including a saturated monovalent hydrocarbon moiety having straight or branched moieties or combinations thereof and containing 1-8 carbon atoms, preferably 1-6 carbon atoms and more preferably 1-4 carbon atoms. Alkyl moieties can optionally be substituted by amino groups, halogens or one methylene (—$CH_2$—) can be replaced by carbonyl, NH, carboxyl or by oxygen.

The term "H" as used herein refers to a hydrogen atom.
The term "O" as used herein refers to an oxygen atom.
The term "N" as used herein refers to a nitrogen atom.
The term "amino" as used herein refers to a group of formula —$NH_2$.
The term "halogen", as used herein refers to an atom of chlorine, bromine, iodine or fluorine.
The term "carbonyl" as used herein refers to a group of formula —C=O.
The term "carboxyl", as used herein refers to a group of formula —C(O)O—.

Compounds of the invention are:
N-(imidazolidin-2-ylidene)quinolin-4-amine;
N-(imidazolidin-2-ylidene)-4-methylquinolin-3-amine;
4-Chloro-N-(imidazolidin-2-ylidene)quinolin-3-amine;
4-Bromo-N-(imidazolidin-2-ylidene)quinolin-3-amine;
N-(imidazolidin-2-ylidene)pyrido[2,3-b]pyrazin-7-amine;
N-(imidazolidin-2-ylidene)-8-methylpyrido[2,3-b]pyrazin-7-amine;
4-Chloro-N-(imidazolidin-2-ylidene)-1,5-naphthyridin-3-amine.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

As used herein, "tautomer" refers to the migration of protons between adjacent single and double bonds. The tautomerization process is reversible. Compounds described herein can undergo any possible tautomerization that is within the physical characteristics of the compound:

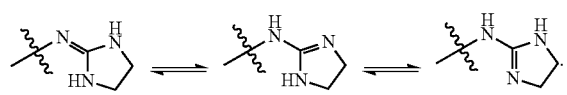 [SMILES: *N=C1NCCN1 ; *NC1=NCCN1 ; *NC1=NCCN1]

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example hydrochloric acid, hydrobromic acid, sulfuric acid, phosphoric acid, nitric acid and the like; or an organic acid for example acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta-Zürich, 2002, 329-345).

The invention also provides a pharmaceutical composition comprising a therapeutically effective amount of the compounds described above and pharmaceutically acceptable carriers, diluents, excipients. In the present invention a "therapeutically effective amount" is any amount of a compound which, when administered to a subject suffering from a disease against which the compounds are effective, causes reduction, remission, or regression of the disease.

The pharmaceutical carrier can be a liquid and the pharmaceutical composition can be in the form of a solution. The pharmaceutically acceptable carrier can be a solid and the composition can be in the form of a powder, capsule or tablet. In a further embodiment, the pharmaceutical carrier can be a gel and the composition can be in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins. Liquid carriers are used in preparing solutions, suspensions, emulsions, syrups, elixirs and pressurized com-positions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary. Such other routes may include, without exception, transdermal, parenteral, subcutaneous, intranasal, via an implant stent, intrathecal, intravitreal, topical to the eye, back of the eye, front of the eye, intramuscular, intravenous, and intrarectal modes of delivery. Additionally, the formulations may be designed to delay release of the active compound over a given period of time, or to carefully control the amount of drug released at a given time during the course of therapy.

In another aspect the invention relates to a method for treating a condition alleviated by alpha 2A, 2B, 2C activation, in a patient in need thereof which comprises administering a pharmaceutical composition comprising a therapeutically effective amount of compound of Formula I or a pharmaceutically acceptable salt thereof.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

In another embodiment of the invention, there is provided an article of manufacture comprising packaging material and a pharmaceutical agent contained within said packaging material, wherein the pharmaceutical agent is therapeutically effective and wherein the packaging material comprises a label which indicates the pharmaceutical agent can be used for treating a disorder associated with the alpha 2 receptors and wherein said pharmaceutical agent comprises an effective amount of at least one compound of Formula I.

Since individual subjects may present a wide variation in severity of symptoms and each drug has its unique therapeutic characteristics, the precise mode of administration and dosage employed for each subject is left to the discretion of the practitioner.

The synthetic scheme set forth below, illustrates how compounds according to the invention can be made. Those skilled in the art will be able to routinely modify and/or adapt the following scheme to synthesize any compounds of the invention covered by Formula I.

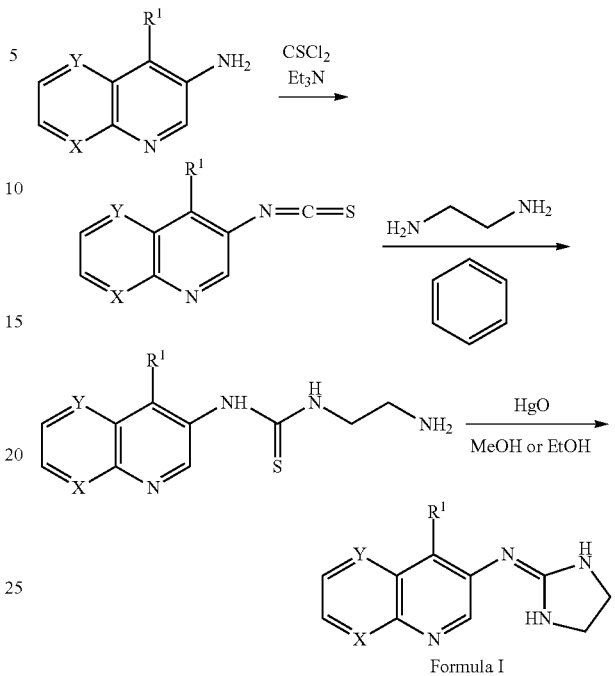

General scheme

The synthesis of compounds of Formula I was started with the pyridine-3-amine derivative, which treated with thiophosgene ($CSCl_2$) in the presence of triethylamine ($Et_3N$) in tetrahydrofuran gave the isothiocyanate key intermediate. The isothiocyanate was then reacted with ethane-1,2-diamine followed by mercury oxide treatment in methanol and afforded the desired compound of Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

The IUPAC names of the compounds mentioned in the examples were generated with ACD version 12.5.

Unless specified otherwise in the examples, characterization of the compounds is performed according to the following methods:

NMR spectra are recorded on 300 MHz Varian and acquired at room temperature. Chemical shifts are given in ppm referenced either to internal TMS or to the residual solvent signal.

All the reagents, solvents, catalysts for which the synthesis is not described are purchased from chemical vendors such as Sigma Aldrich, Fluka, Lancaster, however some known reaction intermediates, for which the CAS registry number is mentioned, were prepared in-house following known procedures.

Usually the compounds of the invention were purified by flash column chromatography.

The following abbreviations are used in the examples:
DCM dichloromethane
EtOH ethanol
MeOH methanol
$NH_3$ ammonia
EtOAc ethylacetate
TEA triethylamine
$CSCl_2$ thiophosgene
THF tetrahydrofuran Example 1

Intermediate 1

1-(2-Aminoethyl)-3-(quinolin-4-yl)thiourea

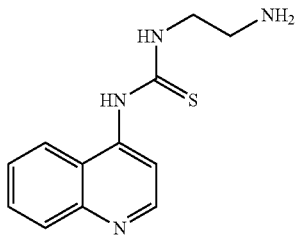 [SMILES: NCCNC(=S)Nc1ccnc2ccccc12]

To a solution of ethane-1,2-diamine (CAS 107-15-3) (704 mg, 4.5 eq) in benzene (10 mL) was added a solution of 4-isothiocyanato-quinoline (CAS 868163-42-2) (480 mg, 2.61 mmol) in benzene (5 mL). The resulting mixture was stirred at room temperature for 16 h. The product precipitated as a pale yellow solid, which was filtered to collect the solid washed with ether and gave Intermediate 1.

Example 2

Intermediate 2

4-Chloro-3-isothiocyanato-1,5-naphthyridine

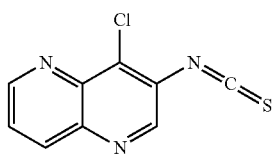 [SMILES: S=C=Nc1cnc2cccnc2c1Cl]

To a solution of 4-chloro-1,5-naphthyridin-3-amine (CAS 930276-73-6) (550 g, 3.07 mmol) in THF (10 mL) was added TEA (0.95 mL, 6.76 mmol) followed by $CSCl_2$ (0.26 mL, 3.4 mmol) at 0° C. The mixture was stirred at room temperature for 2 h. Celite (2 g) was added to the reaction mixture, then concentrated and purified by silica gel column chromatography using hexane:EtOAc (7:3) and gave Intermediate 2 (360 mg).

Example 3

Intermediate 3

1-(2-Aminoethyl)-3-(4-chloro-1,5-naphthyridin-3-yl)thiourea

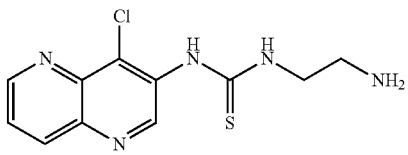 [SMILES: NCCNC(=S)Nc1cnc2cccnc2c1Cl]

To a solution of ethane-1,2-diamine (CAS 107-15-3) (0.54 mL, 8.12 mmol) in benzene (10 mL) was added a solution of Intermediate 2 (360 mg) in benzene (5 mL). The resulting mixture was stirred at room temperature for 16 h. Benzene and excess of ethane-1,2-diamine were decanted. The product was washed with ethyl-ether and yielded Intermediate 3.

Example 4

Compound 1

N-(imidazolidin-2-ylidene)quinolin-4-amine

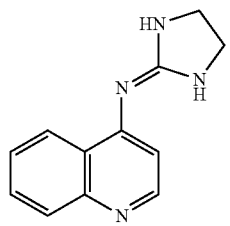 [SMILES: c1ccc2c(N=C3NCCN3)ccnc2c1]

Intermediate 1 was taken in EtOH (15 mL) with mercury oxide (618 mg) and heated at reflux temperature for 4 h. The mixture was cooled to room temperature and filtered through celite. Silica gel was added to the filtrate and concentrated and purified by chromatography on silica gel with 5% $NH_3$-MeOH:DCM and gave (68 mg) Compound 1 as a white solid.

$^1$H NMR (Methanol-$d_6$) δ: 8.54 (d, J=5.0 Hz, 1H), 8.23 (d, J=7.9 Hz, 1H), 7.88 (d, J=8.5 Hz, 1H), 7.61-7.72 (m, 1H), 7.41-7.53 (m, 1H), 7.05 (d, J=5.3 Hz, 1H), 3.56 (s, 4H).

Example 5

Compound 2

4-Chloro-N-(imidazolidin-2-ylidene)-1,5-naphthyridin-3-amine

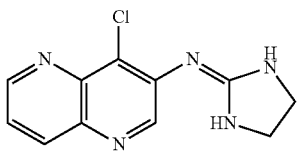 [SMILES: Clc1c(N=C2NCCN2)cnc2cccnc12]

Intermediate 3 was taken in EtOH (15 mL) with mercury oxide (422 mg) and heated at reflux temperature for 2 h. The mixture was cooled to room temperature filtered through celite. Silica gel was added to the filtrate concentrated and purified by silica gel chromatography using 5% $NH_3$-MeOH:DCM and gave (120 mg) Compound 2.

$^1$H NMR (Methanol-$d_4$) δ: 8.90 (dd, J=4.1, 1.5 Hz, 5H), 8.68 (s, 1H), 8.36 (dd, J=8.2, 1.5 Hz, 1H), 7.66 (dd, J=8.5, 4.4 Hz, 1H), 3.56 (s, 4H).

Compounds 3, 4, 5, 6 and 7 were prepared in a similar manner to the method described in Example 5 for Compound 2 starting with the corresponding starting material. The results are tabulated below in Table 1.

TABLE 1

| Compound | IUPAC name | $^1$NMR (Solvent; δ ppm) |
|---|---|---|
| 3 | N-(imidazolidin-2-ylidene)-4-methylquinolin-3-amine | $^1$H-NMR (Methanol-$d_4$) δ: 8.46 (s, 1H), 8.02-8.09 (m, 1H), 7.89-7.98 (m, 1H), 7.51-7.67 (m, 2H), 3.52 (s, 4H), 2.56 (s, 3H) |
| 4 | 4-Chloro-N-(imidazolidin-2-ylidene)quinolin-3-amine | $^1$H NMR (Methanol-$d_4$) δ: 8.55 (s, 1H), 8.14-8.22 (m, 1H), 7.92-8.00 (m, 1H), 7.57-7.68 (m, 2H), 3.52 (s, 4H) |
| 5 | 4-Bromo-N-(imidazolidin-2-ylidene)quinolin-3-amine | $^1$H NMR (Methanol-$d_4$) δ: 8.49 (s, 1H), 8.16-8.23 (m, 1H), 7.92-7.99 (m, 1H), 7.60-7.68 (m, 2H), 3.52 (s, 4H) |
| 6 | N-(imidazolidin-2-ylidene)pyrido[2,3-b]pyrazin-7-amine | $^1$H NMR (Methanol-$d_4$) δ: 8.76-8.85 (m, 3H), 7.88 (d, J = 2.6 Hz, 1H), 3.59 (s, 4H) |
| 7 | N-(imidazolidin-2-ylidene)-8-methylpyrido[2,3-b]pyrazin-7-amine | $^1$H NMR (Methanol-$d_4$) δ: 8.90 (d, J = 1.8 Hz, 4H), 8.85 (d, J = 1.8 Hz, 1H), 8.73 (s, 1H), 3.53 (s, 4H), 2.64 (s, 3H) |

The following assay was used to demonstrate the potency and selectivity of the compounds according to the invention.

Example 6

RSAT Compound Screening

Novel compounds were synthesized and tested for alpha adrenergic activity using the Receptor Selection and Amplification Technology (RSAT) assay (Messier et. al., 1995, Pharmacol. Toxicol. 76, pp. 308-311). Cells expressing each of the alpha 2 adrenergic receptors alone were incubated with the various compounds and a receptor-mediated growth response was measured. The compound's activity was expressed as its relative efficacy compared to a standard full agonist (see Table 2). The compounds of this invention activate alpha 2 receptors.

TABLE 2

Biological Data: Intrinsic Activity $EC_{50}$ nM (efficacy)

| Compound number | IUPAC name | Alpha 2C |
|---|---|---|
| 1 | N-(imidazolidin-2-ylidene)quinolin-4-amine | 17.4 (0.95) |
| 2 | 4-Chloro-N-(imidazolidin-2-ylidene)-1,5-naphthyridin-3-amine | 21 (0.95) |
| 3 | N-(imidazolidin-2-ylidene)-4-methylquinolin-3-amine | 1653 (0.21) |
| 4 | 4-Chloro-N-(imidazolidin-2-ylidene)quinolin-3-amine | 368 (0.66) |
| 5 | 4-Bromo-N-(imidazolidin-2-ylidene)quinolin-3-amine | 1529 (0.17) |
| 6 | N-(imidazolidin-2-ylidene)pyrido[2,3-b]pyrazin-7-amine | 4581 (0.44) |
| 7 | N-(imidazolidin-2-ylidene)-8-methylpyrido[2,3-b]pyrazin-7-amine | 311 (0.93) |

What is claimed is:

1. A method of treating a condition that is alleviated by alpha 2 receptor activation, the method comprising administering to a mammal in need thereof a pharmaceutical composition comprising a therapeutically effective amount of at least one compound of Formula I:

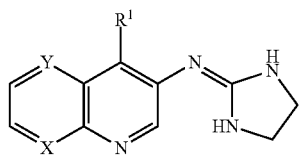

Formula I wherein:
$R^1$ is hydrogen, substituted or unsubstituted $C_{1-8}$ alkyl or halogen;
Y is CH or N; and
X is CH or N;
provided that the compound is not N-(4,5-dihydro-1H-imidazol-2-yl)-3-quinolinamine;
wherein the condition is ocular hypertension or glaucoma.

2. The method according to claim 1, wherein:
$R^1$ is hydrogen, methyl, bromine or chlorine;
Y is CH or N; and
X is CH or N.

3. The method according to claim 1, wherein:
$R^1$ is methyl, bromine or chlorine;
Y is CH or N; and
X is CH or N.

4. The method according to claim 1, wherein:
$R^1$ is methyl;
Y is CH or N; and
X is CH or N.

5. The method according to claim 1, wherein:
$R^1$ is bromine;
Y is CH or N; and
X is CH or N.

6. The method according to claim 1, wherein:
$R^1$ is chlorine;
Y is CH or N; and
X is CH or N.

7. The method according to claim 1, wherein:
$R^1$ is chlorine;
Y is CH or N; and
X is CH.

8. The method according to claim 1, wherein:
$R^1$ is chlorine;
Y is CH; and
X is CH or N.

9. The method according to claim 1, wherein the compound of Formula I is selected from:
N-(imidazolidin-2-ylidene)-4-methylquinolin-3-amine;
4-Chloro-N-(imidazolidin-2-ylidene)quinolin-3-amine;
4-Bromo-N-(imidazolidin-2-ylidene)quinolin-3-amine;
N-(imidazolidin-2-ylidene)pyrido[2,3-b]pyrazin-7-amine;
N-(imidazolidin-2-ylidene)-8-methylpyrido[2,3-b]pyrazin-7-amine; and
4-Chloro-N-(imidazolidin-2-ylidene)-1,5-naphthyridin-3-amine.

* * * * *

UNITED STATES PATENT AND TRADEMARK OFFICE
CERTIFICATE OF CORRECTION

PATENT NO. : 9,199,989 B2  
APPLICATION NO. : 14/332110  
DATED : December 1, 2015  
INVENTOR(S) : Liming Wang et al.

Page 1 of 1

It is certified that error appears in the above-identified patent and that said Letters Patent is hereby corrected as shown below:

On the Title page,

In Item (56), in column 2, under "Other Publications", line 15, delete "Isoteric" and insert -- Isosteric --, therefor.

In Item (56), in column 2, under "Other Publications", line 19, delete "Bromonidine" and insert -- Brimonidine --, therefor.

In the Specification,

In column 2, line 13, delete "cutenous" and insert -- cutaneous --, therefor.

In columns 9-10, in Table 1, line 1, delete "$^1$NMR" and insert -- $^1$H NMR --, therefor.

In columns 9-10, in Table 1, line 2, delete "$^1$H-NMR" and insert -- $^1$H NMR --, therefor.

Signed and Sealed this  
Twelfth Day of July, 2016

Michelle K. Lee  
*Director of the United States Patent and Trademark Office*